United States Patent [19]

Harding et al.

[11] Patent Number: 5,705,144
[45] Date of Patent: Jan. 6, 1998

[54] COSMETIC COMPOSITION CONTAINING RETINOL AND DIOIC ACID

[75] Inventors: Clive Roderick Harding, Rushden; Caroline Marian Lee, Ampthill, both of United Kingdom; Ian Richard Scott, Allendale, N.J.

[73] Assignee: Unilever Patent Holdings B.V., Vlaardingen, Netherlands

[21] Appl. No.: 614,942

[22] Filed: Mar. 11, 1996

Related U.S. Application Data

[63] Continuation of Ser. No. 128,024, Sep. 29, 1993, abandoned.

[30] Foreign Application Priority Data

Sep. 30, 1992 [GB] United Kingdom ............... 9220670

[51] Int. Cl.$^6$ ............... A61K 7/42; A61K 31/20; A61K 31/07
[52] U.S. Cl. ............... 424/59; 514/557; 514/560; 514/574; 514/725; 514/887
[58] Field of Search ............... 424/59, 60; 514/944, 514/887, 560, 557, 574, 725

[56] References Cited

U.S. PATENT DOCUMENTS

| | | | |
|---|---|---|---|
| 4,701,471 | 10/1987 | Loucks, Sr. | 514/887 |
| 4,713,394 | 12/1987 | Thornfeldt | 514/887 |
| 5,002,760 | 3/1991 | Katzev | 514/944 |
| 5,153,230 | 10/1992 | Jaffery | 514/847 |
| 5,215,749 | 6/1993 | Nicoll | 424/401 |
| 5,266,307 | 11/1993 | Voorhees et al. | 424/59 |
| 5,326,790 | 7/1994 | Thornfeldt | 514/784 |

FOREIGN PATENT DOCUMENTS

| | | |
|---|---|---|
| 0117080 | 8/1984 | European Pat. Off. |
| 0158090 | 10/1985 | European Pat. Off. |
| 229654 | 7/1987 | European Pat. Off. |
| 297436 | 1/1989 | European Pat. Off. |
| 3811081 | 10/1989 | Germany |

OTHER PUBLICATIONS

Patent Abstracts of Japan, vol. 16, No. 156 (C-930) Apr. 16, 1992 & JP A 04 009 325, Jan. 1992.

*Primary Examiner*—C. Warren Ivy
*Assistant Examiner*—Evelyn Huang
*Attorney, Agent, or Firm*—Cushman Darby & Cushman IP Group of Pillsbury Madison & Sutro LLP

[57] ABSTRACT

A composition for topical application to human skin in order to promote the repair of photo-damaged skin and/or to reduce or prevent the damaging effects of ultra-violet light on skin and/or to lighten the skin comprising retinol or a derivative thereof and a dioic acid.

9 Claims, No Drawings

COSMETIC COMPOSITION CONTAINING RETINOL AND DIOIC ACID

This is a continuation of application Ser. No. 08/128,024, filed on Sep. 29, 1993, which is abandoned.

FIELD OF INVENTION

The invention relates to a composition for topical application to human skin in order to promote the repair of photo-damaged skin and/or to reduce or prevent the damaging effects of ultra-violet light on skin and/or to lighten the skin. The invention also relates to the use of such compositions in the repair of photo-damaged skin and in the prevention of damage to skin due to exposure to ultra-violet light.

BACKGROUND TO THE INVENTION

The treatment of human skin damaged due to exposure to ultra-violet light, ie photo-damaged, has been subject to much research effort in recent years, particularly with the realisation that skin cancer and other skin disorders can arise where the exposure to sunlight is excessive. This problem is even more serious with the depletion of the ozone layer which is believed to permit a higher level of ultra-violet radiation to reach the earth's surface.

Chronic exposure to sunlight results in multiple adverse effects on all structural elements of the skin. The clinical manifestation of these changes, collectively known as photoageing is lax, dry inelastic skin that is wrinkled and blotchy with a coarse, roughened texture.

Skin blotchiness or mottling (hyperpigmentation) is due to changes in the melanocytes within the population of epidermal cells. These pigment-producing cells, which unlike the keratinocytes remain at the base of the epidermis, lose their normal regulation process with ageing and produce excess pigment. This leads to the formation of dense perinuclear clumps of melanin in slowly turning-over keratinocytes within the epidermis, and areas of hyperpigmentation or "age spots" develop.

In the therapy of such hyperpigmented skin, azelaic acid is known as a skin lightening agent which is effective by inhibiting the formation of melanin. Vitamin A acid (retinoic-acid) is beneficial in hyperpigmentation problems (Bulengo-Ransby S M et al (1993) New England Journal of Medicine pp 1438–1443).

Also, by increasing cell turnover Vitamin A acid prevents accumulation of pigment within the more rapidly dividing and migrating keratinocytes. Vitamin A acid also enhances the pigment-reducing potential of conventional skin lightening agents.

The topical application of Vitamin A acid does however have a major drawback in that it is a skin irritant, and can accordingly damage the skin. Its recommended use for example as a prescription drug in the treatment of acne involves careful control, such that excessive doses are avoided in order to restrict the side effects which can occur with skin. By the same token, the use of Vitamin A acid in the treatment or prevention of photo-damaged skin is severely limited by these side effects.

We have now discovered that retinol or certain derivatives thereof, when combined with certain saturated or unsaturated dioic acids can be used effectively in the repair of photo-damaged skin or the prevention of photo-damage to skin following exposure to ultra-violet light. This combination is also particularly useful in reducing hyperpigmentation of skin or to lighten the skin.

DEFINITION OF THE INVENTION

Accordingly, the invention provides a composition suitable for topical application to human skin in order to promote repair of photo-damaged skin and/or to reduce or prevent the damaging effects of ultra-violet light on skin, and/or to lighten the skin, which composition comprises:

i) an effective amount of from 0.01 to 10% by weight of retinol or a derivative thereof having the structure (1):

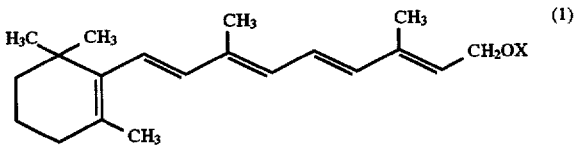

where X represents H or —COR$^1$ where R$^1$ represents a group chosen from branched or unbranched, alkyl or alkenyl groups having an average from 1 to 20 carbon atoms; and ii) an effective amount of from 0.1 to 30% by weight of a dioic acid having the general structure (2)

$$COOH-(C_aH_b)-COOH \qquad (2)$$

where a is an integer of from 6 to 20 and b is an integer of from 8 to 40

The invention further provides a method of reducing or preventing the damaging effects of ultra-violet light on skin and/or of lightening the skin which method includes the topical application of composition comprising:

i) an effective amount of from 0.01 to 10% by weight of retinol or a derivative thereof having the structure (1):

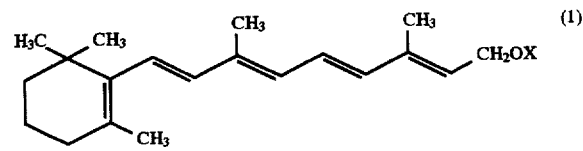

where X represents H or —COR$^1$ where R$^1$ represents a group chosen from branched or unbranched, alkyl or alkenyl groups having an average from 1 to 20 carbon atoms; and ii) an effective amount of from 0.1 to 30% by weight of a dioic acid having the general structure (2)

$$COOH-(C_aH_b)-COOH \qquad (2)$$

where a is an integer of from 6 to 20 and b is an integer of from 8 to 40

DISCLOSURE OF THE INVENTION

The invention concerns a composition comprising retinol or a derivative thereof together with a dioic acid having the general structure (2) which together behave synergistically in reducing skin blotchiness and mottling due to hyperpigmentation. Furthermore, due to the rejuvenating influence of the retinol or its derivative on skin, there will be an overall improvement in skin texture with reduction in fine wrinkling and improved skin colour. Also, co-formulation with a sunscreen will enhance the photo-stability and activity of retinol or its derivative within the formulation and also prevent further actinic damage to all epidermal cells.

Retinol and Derivatives Thereof

The composition according to the invention comprises retinol or a derivative thereof having the structure (1).

In addition to retinol itself, examples of derivatives of retinol include:

Retinyl acetate
Retinyl butyrate
Retinyl propionate
Retinyl octanoate
Retinyl laurate
Retinyl palmitate
Retinyl oleate
Retinyl linoleate The amount of retinol, or a derivative thereof, present in the composition according to the invention is from 0.01 to 10% and preferably 0.05 to 5% by weight of the composition, most preferably 0.05 to 1% by weight of the composition.

Preferably the composition comprises retinol, most preferable the composition comprises the trans-isomer of retinol.

The Dioic Acid

The composition according to the invention also comprises a dioic acid having the general structure (2).

The dioic acid is selected from $C_8$–$C_{22}$ mono- and di-unsaturated dioic acids and $C_8$–$C_{22}$ saturated dioic acids.

Preferably the dioic acid is selected from $C_{9-18}$ saturated, mono- and di-unsaturated dioic acids and mixtures thereof.

The amount of dioic acid which is present in the composition according to the invention is from 0.1 to 30%, preferably from 1 to 25% by weight of the composition, even more preferably from 5 to 20% by weight of the composition. $C_8$–$C_{16}$ saturated dioic acids are available commercially from chemical suppliers.

$C_{17}$–$C_{22}$ saturated or unsaturated dioic acids while not commercially available can be manufactured by fermentation using non-chain shortening Candida yeast β-oxidation mutants. Saturated or unsaturated hydrocarbons, aldehydes, alcohols or monocarboxylic acids are converted to the corresponding chain length dicarboxylic acid by the oxidative action of the mutant yeast. The production and isolation of β-oxidation mutant Candida yeasts and their use for the production of dicarboxylic acids by fermentation has been described in Casey J, Dobb R and Mycock G (1990), J Gen Microbiol, 136, 1197–1202; and Buhler M and Schindler J (1984) in Biotechnology, Volume 6, edited by Rehm H J and Reed G, Verlag Chemie, Weinheim, pp 229–385.

Furthermore we have discovered that $C_8$–$C_{16}$ unsaturated dioic acids may be produced using the method disclosed in EP 341 796. Further detail of this production is provided below.

The unsaturated dioic acids are conveniently produced by biochemical oxidation of non-toxic levels of unsaturated fatty acids using a yeast propagated in a carbon substrate-containing growth medium.

Yeasts suitable for the purpose are disclosed in EP 0341796 and in Casey et al., (1990) Journal of General Microbiology 136, 1197–1202. Such strains (eg *Candida cloacae* 5GLA12, abbreviated to "LA12") exhibit no (or very low levels of) beta-oxidation activity.

Conveniently the yeasts are supplied with unsaturated fatty acids in the form of esters, preferably as triglyceride esters such as oil. Particularly suitable examples include unsaturated oils such as sunflower oil and olive oil, treated to remove free fatty acids.

Preferably the oils used as starting materials are triglycerides in which the predominant unsaturated long chain fatty acid is a $C_{18}$ compound. Fermentation by yeast strains such as LA12 can result in the production of mixtures of chain-shortened, unsaturated dioic acids typically $C_8$ to $C_{16}$ compounds. These mixed products can be separated into fractions, for example by differential solvent extraction.

If one assumes that there is random removal of $C_2$ units during beta-oxidation, and that no isomerisation of the products occurs, the following products may be predicted to be formed when using oleic acid as a substrate:

cis-7-hexadecene dioic acid; cis-5-tetradecene dioic acid; cis-7-tetradecene dioic acid; cis-3-dodecene dioic acid; cis-5-dodecene dioic acid; cis-3-decene dioic acid; cis-5-decene dioic acid and cis-3-octene dioic acid.

From linoleic acid, the following products may be expected:

cis-6, 9-hexadecadiene dioic acid; cis-4, 7-hexadecadiene dioic acid; cis-5, 8-tetracadiene dioic acid; cis-4, 7-tetracadiene dioic acid; cis-3, 6-dodecadiene dioic acid; cis-2, 5-tetradecadiene dioic acid; cis-4, 7-dodecadiene dioic acid; cis-3, 6-decadiene dioic acid; cis-2, 5-decadiene dioic acid; cis-2, 5-dodecadiene dioic acid; cis-2, 5-octadiene dioic acid; cis-4-decene dioic acid and cis-2-octene dioic acid.

Likewise the predicted products using linolenic acid as a starting material are as follows: cis-4, 7, 10-hexadecatriene dioic acid; cis-6, 9, 12-hexadecatriene dioic acid; cis-2, 5, 8-tetradecatriene dioic acid; cis-4, 7, 10-tetradecatriene dioic acid; cis-2, 5, 8-dodecatriene dioic acid; cis-3, 6-dodecadiene dioic acid; cis-2, 5, 8-decatriene dioic acid; cis-3, 6-decadiene dioic acid; cis-4-decene dioic acid; cis-2, 5-octadiene dioic acid; cis-4-octene dioic acid and cis-2-octene dioic acid.

There is a reason to believe that, in each case, a wider range of products may be formed than those predicted. This is because there is evidence to suggest that isomerism of these compounds does occur (Osmundsen & Hovik, 1988, Biochemical Society Transactions 16, 420–422).

Naturally, where trans-unsaturated compounds are the starting compounds, trans-unsaturated products will result.

Some of the products of these fermentations have been extensively characterised. For instance, nuclear magnetic resonance (NMR) spectroscopy has been used to determine the structure of the $C_{12}$ mono-unsaturated dioic acid derived from olive oil. The compound is substantially pure (ie no other isomeric forms are readily apparent) cis-5-dodecene dioic acid.

It is a highly preferred feature that the yeast employed for the process is not propagated under conditions of nitrogen limitation. Instead, the yeast is grown under conditions which are comparatively enriched for nitrogen, wherein alteration of pH affects the chain shortening β-oxidation activity of the organism.

Thus, it is found that the product profile of the fermentation process may conveniently be modified by alteration of the pH of the fermentation medium during the production of unsaturated dioic acids. In particular, it is possible to alter the relative concentrations of the different lengths of dioic acid molecules in this way. For example, by reducing the pH from 7.5 to 7.1 during fermentation of olive oil, it is possible to increase the relative amount of the $C_{12}$ unsaturated dioic acid.

This is significant because certain fractions of the fermentation products may have especially advantageous properties for particular intended uses. For example, the $C_{12}$–$C_{14}$ fraction obtained from the fermentation of olive oil is particularly active in inhibiting the growth of *Propionibacterium acnes*, whilst the $C_8$–$C_{10}$ fraction obtained from the fermentation of sunflower oil is particularly active as a general anti-microbial agent. The different fractions of different products may be obtained from the culture medium by extracting with diethyl ether at different acidic pHs.

Specific example of novel unsaturated dioic acid production: Production of medium chain unsaturated dioic acids by fermentation A beta-oxidation mutant of *Candida cloacae* produced by mutagensis using nitrosoguanidine (mutant LA12, see EP0341796 and see also Casey et al, J Gen Microbiol (1990), 136, 1197–1202) was used to produce $C_8$–$C_{14}$ unsaturated dioic acids from triglycerides such as olive oil and sunflower oil which contain high levels of unsaturated fatty acids.

A chemically defined medium was used as shown below:

| | | |
|---|---|---|
| Sucrose | 20 g/l | autoclave 20 mins at 121° C. |
| $(NH_4)_2HPO_4$ | 6 g/l | |
| $KH_2PO_4$ | 6.4 g/l | |
| $Na_2SO_4$ | 1.5 g/l | |
| Triglyceride (eg olive oil or sunflower oil) | 10–40 ml/l | |
| $ZnSO_4.7H_2O$ | 20 mg/l | filter sterilise and add asceptically when fermenter cool |
| $MnSO_4.4H_2O$ | 20 mg/l | |
| $FeSO_4.7H_2O$ | 20 mg/l | |
| $MgCl_2.6H_2O$ | 2 g/l | |
| Biotin | 100 mg/l | |
| Pantothenate | 6 mg/l | |
| Thiamine | 8 mg/l | |
| Nicotinic acid | 30 mg/l | |
| Pyridoxine | 20 mg/l | |

The fermenter conditions were:

| | | |
|---|---|---|
| Growth pH: | 6.8 | maintained by auto-addition of 10M NaOH |
| Production pH: | 7.4–7.5 | |
| Temperature: | 30° C. | |
| Aeration: | 0.1 v/v/m air | |
| Impeller speed: | 800–1000 rpm | |
| Fermenter volume: | 2.5 L | |
| Inoculum: | 2% | |
| Fermenter type: | LSL fitted with foam breaker | |

The medium (2.5l) was inoculated with 2% (v/v) of a 24 hr culture of *Candida cloacae* beta-oxidation mutant LA12 grown on yeast extract (5 g/l/sucrose (10 g/l), peptone 5 g/l) medium. The culture was grown for 20 hr at pH 6.8 then 20 ml/l of oil was added and the pH increased to 7.4–7.6 to initiate production of the medium chain unsaturated dioic acids. The oil was either sunflower oil or silica-purified olive oil. During production of the dioic acids, the RQ (respiratory quotient) value fell to about 0.6. Aliquots (10–20 ml) of fermenter broth were removed daily for lipid analysis and additional oil was added as required.

The fermentation was harvested when production ceased at 8–12 days.

Medium chain unsaturated dioic acids were isolated from fermenter broths by acidification to pH 6 with HCl then extraction with diethyl ether to isolate a $C_{12}$–$C_{14}$ rich fraction. The broth was then further acidified with HCl to about pH 2.0 and further extracted with diethyl ether to isolate a $C_8$–$C_{10}$ rich fraction. For isolation of the mixed acids the broth pH was decreased from 7.5 to about 2.0 in one step then extracted with diethyl ether. Solvent was removed from the dioic acid fractions by rotary evaporation. Specific example of use of pH to alter dioic acid production profile At a production pH of 7.4–7.6 the dominant species from oils (e.g. olive oil) containing $C_{18}$ unsaturated fatty acids is the $C_{14}$ unsaturated dioic acid.

However, if the production pH is decreased from 7.4–7.6 to around 7.1, the $C_{12}$ unsaturated dioic acid becomes the dominant species. Fermentation was performed as detailed in the above examples until fermentation day 8 when the pH was dropped to 7.1 resulting in 'turn-over' of the $C_{14}$ species and an increase in $C_{12}$ production.

The Cosmetically Acceptable Vehicle

The composition according to the invention also comprises a cosmetically acceptable vehicle to act as a diluent, dispersant or carrier for other materials present in the composition, so as to facilitate their distribution when the composition is applied to the skin.

Vehicles other than water can include liquid or solid emollients, solvents, humectants, thickeners and powders. Examples of each of these types of vehicle, which can be used singly or as mixtures of one or more vehicles, are as follows:

Emollients, such as stearyl alcohol, glyceryl monoricinoleate, mink oil, cetyl alcohol, isopropyl isostearate, stearic acid, isobutyl palmitate, isocetyl stearate, oleyl alcohol, isopropyl laurate, hexyl laurate, decyl oleate, octadecan-2-ol, isocetyl alcohol, eicosanyl alcohol, behenyl alcohol, cetyl palmitate, silicone oils such as dimethylpolysiloxane, di-n-butyl sebacate, isopropyl myristate, isopropyl palmitate, isopropyl stearate, butyl stearate, polyethylene glycol, triethylene glycol, lanolin, cocoa butter, corn oil, cotton seed oil, olive oil, palm kernel oil, rapeseed oil, safflower seed oil, evening primrose oil, soybean oil, sunflower seed oil, avocado oil, sesame seed oil, coconut oil, arachis oil, castor oil, acetylated lanolin alcohols, petroleum jelly, mineral oil, butyl myristate, isostearic acid, palmitic acid, isopropyl linoleate, lauryl lactate, myristyl lactate, decyl oleate, myristyl myristate;

Propellants, such as air, propane, butane, isobutane, dimethyl ether, carbon dioxide, nitrous oxide;

Solvents, such as ethyl alcohol, isopropanol, acetone, ethylene glycol monoethyl ether, diethylene glycol monobutyl ether, diethylene glycol monoethyl ether;

Powders, such as chalk, talc, fuller's earth, kaolin, starch, gums, colloidal silica sodium polyacrylate, tetra alkyl and/or trialkyl aryl ammonium smectites, chemically modified magnesium aluminium silicate, organically modified montmorillonite clay, hydrated aluminium silicate, fumed silica, carboxyvinyl polymer, sodium carboxymethyl cellulose, ethylene glycol monostearate.

The cosmetically acceptable vehicle will usually form from 10 to 99.9%, preferably from 50 to 99% by weight of the emulsion, and can, in the absence of other cosmetic adjuncts, form the balance of the emulsion.

Organic Sunscreens

The composition of the invention optionally can comprise an organic sunscreen further to enhance the benefit of the composition in providing protection from the harmful effects of excessive exposure to sunlight.

Examples of suitable organic sunscreens, when required, include those set out in Table 1 below, and mixtures thereof.

TABLE 1

| CTFA Name | Trade Name | Supplier |
|---|---|---|
| Benzophenone-3 | UVINUL M-40 | BASF Chemical Co |
| Benzophenone-4 | UVINUL MS-40 | BASF Chemical Co |
| Benzophenone-8 | SPECTRA-SORB UV-24 | American Cyanamide |
| DEA Methoxycinnamate | BERNEL HYDRO | Bernal Chemical |
| Ethyl dihydroxy-propyl-PABA | AMERSCREEN P | Amerchol Corp |
| Glyceryl PABA | NIPA GMPA | Nipa Labs |
| Homosalate | KEMESTER HMS | Hunko Chemical |
| Methyl anthranilate | SUNAROME UVA | Felton Worldwide |
| Octocrylene | UVINUL N-539 | BASF Chemical Co |
| Octyl dimethyl | PABA AMERSCOL | Amerchol Corp |
| Octyl methoxy-cinnamate | PARSOL MCX | Bernel Chemical |

TABLE 1-continued

| CTFA Name | Trade Name | Supplier |
| --- | --- | --- |
| Octyl salicylate | SUNAROME WMO | Felton Worldwide |
| PABA | PABA | National Starch |
| 2-Phenyl-benzimidazole--5-sulphonic acid | EUSOLEX 232 | EM Industries |
| TEA salicylate | SUNAROME W | Felton Worldwide |
| 3-(4-methylbenzy-lidene)-camphor | EUSOLEX 6300 | Em Industries |
| Benzophenone-1 | UVINUL 400 | BASF Chemical Co |
| Benzophenone-2 | UVINUL D-50 | BASF Chemical Co |
| Benzophenone-6 | UVINUL D-49 | BASF Chemical Co |
| Benzophenone-12 | UVINUL 408 | BASF Chemical Co |
| 4-Isopropyl dibenzoyl methane | EUSOLEX 8020 | EM Industries |
| Butyl methoxy di-benzoyl methane | PARSOL 1789 | Givaudan Corp |
| Etocrylene | UVINUL N-35 | BASF Chemical Co |

The composition of the invention can accordingly comprise from 0.1 to 10%, preferably from 1 to 5% by weight of an organic sunscreen material.

Inorganic Sunscreen

The composition according to the invention optionally can also comprise as a sunscreen ultrafine titanium dioxide in either of two forms, namely water-dispersible titanium dioxide and oil-dispersible titanium dioxide.

Water-dispersible titanium dioxide is ultrafine titanium dioxide, the particles of which are uncoated or which are coated with a material to impart a hydrophilic surface property to the particles. Examples of such materials include aluminium oxide and aluminium silicate.

Oil-dispersible titanium dioxide is ultrafine titanium dioxide, the particles of which exhibit a hydrophobic surface property, and which, for this purpose, can be coated with metal soaps such as aluminium stearate, aluminium laurate or zinc stearate, or with organosilicone compounds.

By "ultrafine titanium dioxide" is meant particles of titanium dioxide having an average particle size of less than 100 nm, preferably from 10 to 40 nm and most preferably from 15 to 25 nm.

By topical application to the skin of a mixture of both water-dispersible ultrafine titanium dioxide and oil-dispersible ultrafine titanium dioxide, synergically enhanced protection of the skin against the harmful effects of both UV-A and UV-B rays is achievable.

It is believed that this unexpected benefit is due to the deposition of each type of titanium dioxide on different regions of the skin surface, water-dispersible titanium dioxide being preferentially retained by hydrophilic regions of the skin's surface, while oil-dispersible titanium dioxide is retained preferentially by hydrophobic regions of the skin's surface. The combined overall effect is that more efficient physical coverage of the skin's surface is attainable and this can be demonstrated by measurement of the Sun Protection Factor (SPF).

In order to achieve the enhanced, synergistic benefit, as herein described, the weight ratio of water-dispersible titanium dioxide to oil-dispersible titanium dioxide should be from 1:4 to 4:1, preferably from 1:2 to 2:1 and ideally about equal weight proportions.

The total amount of titanium dioxide that can optionally can be incorporated in the composition according to the invention is from 1 to 25%, preferably from 2 to 10% and ideally from 3 to 7% by weight of the composition.

Other Inorganic Sunscreens

The emulsion of the invention optionally can comprise an inorganic sunscreen in addition to ultrafine titanium dioxide as herein defined.

Examples of other inorganic sunscreens include:

zinc oxide, having an average particle size of from 1 to 300 nm, iron oxide, having an average particle size of from 1 to 300 nm, silica, such as fumed silica, having an average particle size of from 1 to 100 nm.

It should be noted that silica, when used as an ingredient in the emulsion according to the invention can provide protection from infra-red radiation.

Other Skin-whitening Agents

Compositions according to the invention may also optionally comprise other skin whitening agents.

Examples of skin-lightening agents include:

L-ascorbic acid, and derivatives thereof

Kojic acid, and derivatives thereof

Hydroquinone

Extract of placenta

Arbutin

Niacin

Niacinamide, and

Compounds having the structure (3)

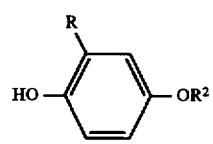

(3)

where $R^1$ represents H, or an ether group represented by $OR^3$, $R^2$ and $R^3$ are the same or different and each represents a group chosen from branched or unbranched alkyl or alkenyl groups having an average of from 1 to 20 carbon atoms.

OPTIONAL SKIN BENEFIT MATERIALS AND COSMETIC ADJUNCTS

A particularly convenient form of the composition according to the invention is an emulsion, in which case an oil or oily material will normally be present, together with an emulsifier to provide either a water-in-oil emulsion or an oil-in-water emulsion, depending largely on the average hydrophilic-lipophilic balance (HLB) of the emulsifier employed.

Oil or Oily Material

The composition according to the invention can optionally comprise one or more oils or other materials having the properties of an oil.

Examples of suitable oils include mineral oil and vegetable oils, and oil materials, such as those already proposed herein as emollients. Other oils or oily materials include silicone oils, both volatile and non-volatile, such as polydimethyl siloxanes.

The oil or oily material, when present for the purposes for forming an emulsion, will normally form up to 90%, preferably from 10 to 80% by volume of the composition.

Emulsifier

The composition according to the invention can also optionally comprise one or more emulsifiers the choice of which will normally determine whether a water-in-oil or and oil-in-water emulsion is formed.

When a water-in-oil emulsion is required, the chosen emulsifier or emulsifiers should normally have an average HLB value of from 1 to 6. When an oil-in-water emulsion is required, a chosen emulsifier or emulsifiers should have an average HLB value of >6.

Examples of suitable emulsifiers are set below in Table 2 in which the chemical name of the emulsifiers is given together with an example of a trade name as commercially available, and the average HLB value.

TABLE 2

| Chemical Name of Emulsifier | Trade Name | HLB Value |
|---|---|---|
| Sorbitan trioleate | Arlacel 85 | 1.8 |
| Sorbitan tristearate | Span 65 | 2.1 |
| Glycerol monooleate | Aldo MD | 2.7 |
| Glycerol monostearate | Atmul 84S | 2.8 |
| Glycerol monolaurate | Aldo MC | 3.3 |
| Sorbitan sesquioleate | Arlacel 83 | 3.7 |
| Sorbitan monooleate | Arlacel 80 | 4.3 |
| Sorbitan monostearate | Arlacel 60 | 4.7 |
| Poloxyethylene (2) stearyl ether | Brij 72 | 4.9 |
| Poloxyethylene sorbitol beeswax derivative | G-1702 | 5 |
| PEG 200 dilaurate | Emerest 2622 | 6.3 |
| Sorbitan monopalmitate | Arlacel 40 | 6.7 |
| Polyoxyethylene (3.5) nonyl phenol | Emulgen 903 | 7.8 |
| PEG 200 monostearate | Tegester PEG 200 MS | 8.5 |
| Sorbitan monolaurate | Arlacel 200 | 8.6 |
| PEG 400 dioleate | Tegester PEG 400-DO | 8.8 |
| Polyoxyethylene (5) monostearate | Ethofat 60-16 | 9.0 |
| Polyoxyethylene (4) sorbitan monostearate | Tween 61 | 9.6 |
| Polyoxyethylene (4) lauryl ether | Brij 30 | 9.7 |
| Polyoxyethylene (5) sorbitan monooleate | Tween 81 | 10.0 |
| PEG 300 monooleate | Neutronyx 834 | 10.4 |
| Polyoxyethylene (20) sorbitan tristearate | Tween 65 | 10.5 |
| Polyoxyethylene (20) sorbitan trioleate | Tween 85 | 11.0 |
| Polyoxyethylene (8) monostearate | Myrj 45 | 11.1 |
| PEG 400 monooleate | Emerest 2646 | 11.7 |
| PEG 400 monostearate | Tegester PEG 400 | 11.9 |
| Polyoxyethylene 10 monooleate | Ethofat 0/20 | 12.2 |
| Polyoxyethylene (10) stearyl ether | Brij 76 | 12.4 |
| Polyoxyethylene (10) cetyl ether | Brij 56 | 12.9 |
| Polyoxyethylene (9.3) octyl phenol | Triton X-100 | 13.0 |
| Polyoxyethylene (4) sorbitan monolaurate | Tween 21 | 13.3 |
| PEG 600 monooleate | Emerest 2660 | 13.7 |
| PEG 1000 dilaurate | Kessco | 13.9 |
| Polyoxyethylene sorbitol lanolin derivative | G-1441 | 14.0 |
| Polyoxyethylene (12) lauryl ether | Ethosperse LA-12 | 14.4 |
| PEG 1500 dioleate | Pegosperse 1500 | 14.6 |
| Polyoxyethylene (14) laurate | Arosurf HFL-714 | 14.8 |
| Polyoxyethylene (20) sorbitan monostearate | Tween | 14.9 |
| Polyoxyethylene 20 sorbitan monooleate | Tween 80 | 15.0 |
| Polyoxyethylene (20) stearyl ether | Brij 78 | 15.3 |
| Polyoxyethylene (20) sorbitan monopalmitate | Tween 40 | 15.6 |
| Polyoxyethylene (20) cetyl ether | Brij 58 | 15.7 |
| Polyoxyethylene (25) oxypropylene monostearate | G-2162 | 16.0 |
| Polyoxyethylene (20) sorbitol monolaurate | Tween 20 | 16.7 |

TABLE 2-continued

| Chemical Name of Emulsifier | Trade Name | HLB Value |
|---|---|---|
| Polyoxyethylene (23) lauryl ether | Brij 35 | 16.9 |
| Polyoxyethylene (50) monostearate | Myrj 53 | 17.9 |
| PEG 4000 monostearate | Pegosperse 4000 MS | 18.7 |

The foregoing list of emulsifiers is not intended to be limiting and merely exemplifies selected emulsifiers which are suitable for use in accordance with the invention.

It is to be understood that two or more emulsifiers can be employed if desired.

The amount of emulsifier or mixtures thereof, that optionally can be incorporated in the composition of the invention is from 1 to 50%, preferably from 2 to 20% and most preferably from 2 to 10% by weight of the composition.

Water

The composition of the invention can also comprise water, usually up to 80%, preferably from 5 to 80% by volume.

Silicone Surfactant

The composition of the invention can also optionally comprise a high molecular weight silicone surfactant which can also act as an emulsifier, in place of or in addition to the optional emulsifier(s) already mentioned.

The silicone surfactant is a high molecular weight polymer of dimethyl polysiloxane with polyoxyethylene and/or polyoxypropylene side chains having a molecular weight of from 10,000 to 50,000 and having the structure:

$$CH_3-\underset{\underset{CH_3}{|}}{\overset{\overset{CH_3}{|}}{Si}}-O-\left[\underset{\underset{R^1}{|}}{\overset{\overset{CH_3}{|}}{Si}}-O\right]_x\left[\underset{\underset{R''}{|}}{\overset{\overset{CH_3}{|}}{Si}}-O\right]_y\underset{\underset{CH_3}{|}}{\overset{\overset{CH_3}{|}}{Si}}-CH_3$$

where the groups R' and R" are each chosen from —H, $C_{1-18}$ alkyl and $$-[CH_2CH_2O]_c[CH_2\underset{\underset{CH_3}{|}}{CHO}]_dH$$

c has a value of from 9 to 115, d has a value of from 0 to 50, x has a value of from 133 to 673, y has a value of from 25 to 0.25.

Preferably, the dimethyl polysiloxane polymer is one in which:

c has a value of from 10 to 114 d has a value of from 0 to 49 x has a value of from 388 to 402 y has a value of from 15 to 0.75 one of groups R' and R" being lauryl, and the other having a molecular weight of from 1000 to 5000.

A particularly preferred dimethyl polysiloxane polymer is one in which:

c has the value 14 d has the value 13 x has the value 249 y has the value 1.25

The dimethyl polysiloxane polymer is conveniently provided as a dispersion in a volatile siloxane, the dispersion comprising, for example, from 1 to 20% by volume of the polymer and from 80 to 99% by volume of the volatile siloxane. Ideally, the dispersion consists of a 10% by volume of the polymer dispersed in the volatile siloxane.

Examples of the volatile siloxanes in which the polysiloxane polymer can be dispersed include polydimethyl siloxane (pentamer and/or hexamer).

A particularly preferred silicone surfactant is cyclomethicone and dimethicone copolyol, such as DC 3225C Formulation Aid available from DOW CORNING. Another is laurylmethicone copolyol, such as DC Q2-5200, also available from Dow Corning.

The amount of silicone surfactant, when present in the composition will normally be up to 25%, preferably from 0.5 to 15% by weight of the emulsion.

Other Cosmetic Adjuncts

Examples of conventional adjuncts which can optionally be employed include preservatives, such as para-hydroxy benzoate esters; antioxidants, such butylated hydroxytoluene; humectants, such as glycerol, sorbitol, 2-pyrrolidone-5-carboxylic acid, dibutylphthalate, gelatin, polyethylene glycol, such as PEG 200–600; buffers, such as lactic acid together with a base such as triethanolamine or sodium hydroxide; waxes, such as beeswax, ozokerite wax, paraffin wax; plant extracts, such as aloe vera, cornflower, witch hazel, elderflower, cucumber; thickeners; activity enhancers; colourants; and perfumes. Cosmetic adjuncts can form the balance of the composition.

Use of the Composition

The composition according to the invention is intended primarily as a skin-care product for topical application to human skin to repair photo-damaged skin and to prevent photo-damage to skin due to exposure to sunlight. In particular, the composition can be used to reduce skin blotchiness and mottling due to hyperpigmentation, to improve skin texture with reductions in fine wrinkling and otherwise to improve skin colour. In general, the composition, when topically applied to skin, is useful in the prevention and or treatment of actinic damage to all epidermal cells.

Test Method—In Vitro Melanocyte Cell Culture

Pigment producing cells derived from a mammalian melanoma are grown in culture by standard methods. Preferred cell lines are B16 or S-91 cells, but other lines or primary mouse or human melanocytes can be used.

Melanoma cells are grown in cell culture medium such as RPMI 1640 (GIBCO) supplemented with fetal calf serum and glutamine to approximately ⅓ confluence. The active is dissolved in culture medium, the pH adjusted as required and sterile filtered. The solution is then added to the cells.

The cells are cultured for a further period of 4 days and the amount of melanin produced assayed by measuring the absorbance at 540 nm of the melanin released into the medium.

Cell viability is tested using neutral red (3-amino-7-dimethylamino-2-methyl phenazine hydrochloride) a water soluble vital dye which passes through the intact plasma membrane and becomes concentrated in lysosomes of viable cells. For any culture, the amount of dye taken up is proportional to the number of viable cells and agents that damage cell and lysosomal membranes inhibit dye incorporation.

The cells are incubated in 50 µg/ml neutral red solution for 3 hours at 37° C. in 5% $CO_2$ in air. The solution is aspirated, the cells washed once in saline and to them added a solvent (50% $H_2O$, 49% ethanol, 1% acetic acid) to solubilise the dye. The amount of neutral red dye is quantified by measuring absorbance at 540 nm.

Results

The above procedure was used to assess the ability of compositions of dioic acids (at a range of concentrations) and retinol (at a range of concentrations) to reduce the amount of melanin produced without affecting cell viability.

These compositions were compared with compositions having retinol alone at a range of concentrations and dioic acids alone at a range of concentrations.

The results for both viability and melanin production were calculated as percentages of the control which contained medium alone. Results are given in Tables 3–7.

Results clearly show that dioic acids and retinol act synergistically to reduce melanin production. There were no effects on cell viability at these concentrations.

TABLE 3

| Trans retinol | $C_9$ Dioic Acid (mM) | | | |
|---|---|---|---|---|
| (mM) | 0 | 0.04 | 0.1 | 1.0 |
| 0 | 100 | 126 ± 3.5 | — | 0 ± 0.1 |
| 0.04 | 176 ± 1.7 | 178 ± 2.5 | 154 ± 8.3 | — |
| 0.05 | 155 ± 9.2 | 70 ± 12.0 | 71 ± 9.0 | — |

TABLE 4

| Trans retinol | $C_{12}$ Dioic Acid (mM) | | | |
|---|---|---|---|---|
| (mM) | 0 | 0.005 | 0.05 | 0.7 |
| 0 | 100 | 98 ± 0.5 | 97 ± 0.6 | 0 ± 0.2 |
| 0.05 | 59 ± 3.0 | 20 ± 4.1 | 23 ± 3.5 | — |

TABLE 5

| Trans retinol | $C_{12:1}$ Dioic Acid and $C_{14:1}$ Dioic Acid (mM) | | | |
|---|---|---|---|---|
| (mM) | 0 | 0.4 | 0.5 | 0.7 |
| 0 | 100 | 113 ± 1.1 | 109 ± 8.1 | 1.1 ± 0.1 |
| 0.04 | — | 143 ± 1.9 | 141 ± 2.6 | — |
| 0.05 | 155 ± 9.1 | 144 ± 1.7 | 24 ± 2.2 | — |

TABLE 6

| Trans retinol | $C_{14:2}$ Dioic Acid (mM) | | | |
|---|---|---|---|---|
| (mM) | 0 | 0.2 | 0.25 | 0.7 |
| 0 | 100 | 102 ± 2.6 | 100 ± 0.6 | 0 ± 0.4 |
| 0.04 | — | 126 ± 1.9 | 114 ± 2.0 | — |
| 0.05 | 156 ± 9.1 | 101 ± 2.0 | 0 ± 0.5 | — |

TABLE 7

| Trans retinol (mM) | $C_{18}$ Dioic Acid (mM) | | | |
| --- | --- | --- | --- | --- |
| | 0 | 0.15 | 0.2 | 0.3 |
| 0 | 100 | 107 ± 2.3 | 100 ± 5.8 | 0.5 ± 0.2 |
| 0.04 | — | 136 ± 0.8 | 137 ± 2.1 | — |
| 0.05 | 155 ± 9.1 | 136 ± 4.4 | 0 ± 0.4 | — |

EXAMPLES

The invention is further illustrated by the following examples; in each formulation, the titanium dioxide employed was ultrafine titanium dioxide having a mean particle size of from 15 to 25 nm.

Example 1

This example illustrates a lotion according to the invention.

| Ingredient | % w/w |
| --- | --- |
| retinyl propionate | 1 |
| azelaic acid | 20 |
| silicone surfactant | 10 |
| volatile siloxane | 14 |
| mineral oil | 1.5 |
| titanium dioxide (water-dispersible) | 2.5 |
| titanium dioxide (oil-dispersible) | 2.5 |
| 2-hydroxyoctanoic acid | 1 |
| 2-hydroxypropanoic acid | 5 |
| butylene glycol | 10 |
| sodium chloride | 2 |
| 1-proline | 0.1 |
| neutralising agent | qs |
| preservative | qs |
| perfume | qs |
| water | qs |

Example 2

This example illustrates a fluid cream according to the invention.

| Ingredient | % w/w |
| --- | --- |
| retinyl acetate | 0.3 |
| $C_{18}$ mono-unsaturated dioic acid | 20 |
| volatile siloxane (DC 345) | 8.2 |
| silicone surfactant (DC 3225C) | 12 |
| petroleum jelly | 0.5 |
| mineral oil | 1.5 |
| Parsol MCX (octyl methoxycinnamate) | 3 |
| titanium dioxide (oil-dispersible) | 2 |
| titanium dioxide (water-dispersible) | 2 |
| sodium chloride | 2 |
| butylene glycol | 10 |
| 1-proline | 0.1 |
| 2-hydroxyoctanoic acid | 1 |
| 2-hydroxypropanoic acid | 5 |
| neutralising agent | qs |
| preservative | qs |
| perfume | qs |
| water | qs |

Example 3

This example illustrates a cream according to the invention.

| Ingredient | % w/w |
| --- | --- |
| retinyl palmitate | 1 |
| azelaic acid | 15 |
| volatile siloxane (DC 345 Fluid) | 8.2 |
| silicone surfactant (DC 3225C) | 12 |
| mineral oil | 1.5 |
| petroleum jelly | 0.5 |
| Parsol MCX (octyl methoxycinnamate) | 1.5 |
| titanium dioxide (oil-dispersible) | 1.0 |
| titanium dioxide (water-dispersible) | 1 |
| 2-hydroxyoctanoic acid | 1 |
| 2-hydroxypropanoic acid | 5 |
| sodium chloride | 2 |
| butylene glycol | 10 |
| 1-proline | 0.1 |
| neutralising agent (aqueous phase to 4.5) | qs |
| preservative | qs |
| perfume | qs |
| water | to 100 |

Example 4

This example illustrates a lotion according to the invention.

| Ingredient | % w/w |
| --- | --- |
| retinyl linoleate | 0.5 |
| retinyl palmitate | 0.5 |
| $C_{18}$ di-unsaturated dioic acid | 20 |
| silicone surfactant (DC 3225C) | 10 |
| volatile siloxane (DC 345) | 14 |
| mineral oil | 1.5 |
| Parsol MCX | 3 |
| titanium dioxide (oil-dispersible) | 2 |
| titanium dioxide (water-dispersible) | 2 |
| butylene glycol | 10 |
| sodium chloride | 2 |
| 1-proline | 0.1 |
| 2-hydroxyoctanoic acid | 1 |
| 2-hydroxypropanoic acid | 5 |
| neutralising agent | qs |
| perfume | qs |
| preservative | qs |
| water | qs |

Example 5

This example illustrates a sunscreen cream in accordance with the invention.

| Ingredient | % w/w |
| --- | --- |
| retinyl oleate | 2 |
| retinyl acetate | 1 |
| $C_{12}$ mono-unsaturated dioic acid | 10 |
| $C_{14}$ mono-unsaturated dioic acid | 10 |
| Polyoxyethylene (2) stearyl alcohol | 3 |
| Polyoxyethylene (21) stearyl alcohol | 2 |
| cetyl alcohol | 1.5 |
| soft white paraffin | 1.5 |
| silicone fluid 200 | 5 |
| liquid paraffin | 8 |
| glycerin | 2 |
| preservatives | 0.5 |
| titanium dioxide (water-dispersible) | 2.5 |
| titanium dioxide (oil-dispersible) | 2.5 |
| water | to 100 |

Example 6

This example also illustrates a sunscreen cream in accordance with the invention.

| Ingredients | % w/w |
|---|---|
| retinyl acetate | 0.2 |
| retinyl laurate | 2 |
| $C_{14}$ di-unsaturated dioic acid | 20 |
| cetyl dimethicone copolyol } * | |
| cetyl dimethicone } * | 5 |
| polyglyceryl-3-oleate } * | |
| hexyl laurate } * | |
| isopropyl myristate | 13.5 |
| beeswax | 3 |
| silicone fluid 200 | 5 |
| preservatives | 0.5 |
| titanium dioxide (water-dispersible) | 2.5 |
| titanium dioxide (oil-dispersible) | 2.5 |
| water | to 100 |

*available is ABIL W508 ex Goldschmidt

Example 7

This example illustrates a lotion according to the invention.

| Ingredient | % w/w |
|---|---|
| retinyl octanoate | 2 |
| $C_{14}$ mono-unsaturated dioic acid | 20 |
| silicone surfactant | 10 |
| volatile siloxane | 14 |
| mineral oil | 1.5 |
| ultrafine titanium dioxide (water-dispersible) | 5 |
| 2-hydroxyoctanoic acid | 1 |
| 2-hydroxypropanoic acid | 5 |
| butylene glycol | 10 |
| sodium chloride | 2 |
| amino acid | 0.1 |
| neutralising agent | qs |
| preservative | qs |
| perfume | qs |
| water | qs |

Example 8

This example illustrates a lotion according to the invention.

| Ingredient | % w/w |
|---|---|
| retinyl palmitate | 2 |
| $C_{22}$ mono-unsaturated dioic acid | 20 |
| silicone surfactant | 10 |
| volatile siloxane | 14 |
| mineral oil | 1.5 |
| ultrafine titanium dioxide (oil-dispersible) | 5 |
| 2-hydroxyoctanoic acid | 1 |
| 2-hydroxypropanoic acid | 5 |
| butylene glycol | 10 |
| sodium chloride | 2 |
| amino acid | 0.1 |
| neutralising agent | qs |
| preservative | qs |
| perfume | qs |
| water | qs |

Example 9

This example illustrates a lotion according to the invention.

| Ingredient | % w/w |
|---|---|
| retinyl octanoate | 1 |
| retinyl linoleate | 1 |
| $C_8$ mono-unsaturated dioic acid | 15 |
| silicone surfactant | 10 |
| volatile siloxane | 14 |
| mineral oil | 1.5 |
| ultrafine titanium dioxide (water-dispersible) | 2.5 |
| ultrafine titanium dioxide (oil-dispersible) | 2.50 |
| 2-hydroxyoctanoic acid | 1 |
| 2-hydroxypropanoic acid | 5 |
| butylene glycol | 10 |
| sodium chloride | 2 |
| amino acid | 0.1 |
| neutralising agent | qs |
| preservative | qs |
| perfume | qs |
| water | qs |

We claim:

1. A composition suitable for topical application to human skin in order to promote skin lightening, repair of photodamaged skin and to reduce or prevent the damaging effects of ultra-violet light on skin, which composition comprises a synergistically effective mixture of:

i) an effective amount of from 0.01 to 10% by weight of retinol or a derivative thereof having the structure (1):

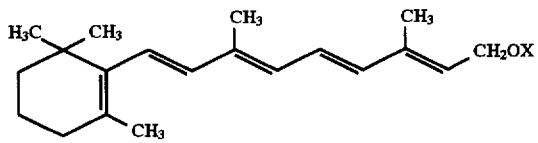

(1)

where X represents H or —$COR^1$ $R^1$ represents a group chosen from branched or unbranched, alkyl or alkenyl groups having an average of from 1 to 20 carbon atoms; and ii) an effective amount of from 0.1 to 30% by weight of a dioic acid having the general structure (2)

$$COOH—(C_aH_b)—COOH \qquad (2)$$

where a is an integer of from 6 to 20 and b is an integer of from 8 to 40.

2. A composition according to claim 1 wherein the amount of retinol or a derivative thereof having the structure (1) is from 0.05 to 5% by weight of the composition.

3. A composition according to claim 1 wherein the amount of retinol or a derivative thereof having the structure (1) is from 0.05 to 1% by weight of the composition.

4. A composition according to claim 1 wherein the amount of dioic acid is from 1 to 25% by weight of the composition.

5. A composition according to claim 1 wherein the amount of dioic acid is from 5 to 20% by weight of the composition.

6. A composition according to claim 1 wherein the dioic acid is selected from the group consisting of $C_9$ to $C_{18}$ saturated, mono- and di-unsaturated dioic acids and mixtures thereof.

7. A composition according to claim 1 wherein the composition comprises trans-retinol.

8. A method for promoting skin lightening, repairing photo-damaged skin and for reducing or preventing the damage to skin due to exposure to ultra-violet light which comprises topically applying an effective amount of the composition of claim 1 to the skin which is damaged or subject to such damage by exposure to ultra-violet light.

9. A composition according to claim 1 including a 1-25% by weight of the composition, of a mixture of water-dispersible and oil-dispersible ultrafine titanium dioxide particles.

* * * * *